(12) United States Patent
Kennedy, II

(10) Patent No.: US 7,811,245 B2
(45) Date of Patent: Oct. 12, 2010

(54) OBJECT-DELIVERY SHUTTLE

(75) Inventor: Kenneth C. Kennedy, II, Clemmons, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 279 days.

(21) Appl. No.: 11/408,577

(22) Filed: Apr. 21, 2006

(65) Prior Publication Data
US 2006/0258974 A1 Nov. 16, 2006

Related U.S. Application Data

(60) Provisional application No. 60/674,632, filed on Apr. 25, 2005.

(51) Int. Cl.
*A61M 31/00* (2006.01)
(52) U.S. Cl. .............................. 604/57; 604/59; 604/60; 604/64; 604/264
(58) Field of Classification Search .............. 604/890.1, 604/891.1, 36, 57, 59–64, 264, 265, 285, 604/288, 288.04
See application file for complete search history.

(56) References Cited

U.S. PATENT DOCUMENTS

| 5,181,505 | A | * | 1/1993 | Lew et al. ............... 128/200.26 |
| 5,507,807 | A | * | 4/1996 | Shippert ......................... 623/8 |
| 6,292,678 | B1 | * | 9/2001 | Hall et al. .................... 600/374 |
| 6,496,561 | B1 | | 12/2002 | Meyer et al. |
| 2003/0135153 | A1 | * | 7/2003 | Hagemeier ................... 604/59 |
| 2003/0158511 | A1 | * | 8/2003 | Shue ........................... 604/17 |
| 2004/0215169 | A1 | * | 10/2004 | Li ............................... 604/537 |
| 2005/0113855 | A1 | * | 5/2005 | Kennedy et al. ............ 606/185 |

FOREIGN PATENT DOCUMENTS

| DE | 31 15763 A1 | 11/1982 |
| WO | WO 01/76525 A2 | 10/2001 |

* cited by examiner

*Primary Examiner*—Kevin C Sirmons
*Assistant Examiner*—Bhisma Mehta
(74) *Attorney, Agent, or Firm*—Brinks Hofer Gilson Lione

(57) ABSTRACT

An object-delivery shuttle for delivering an object over an elongate medical device, such as a wire guide, to a desired location within a body.

15 Claims, 6 Drawing Sheets

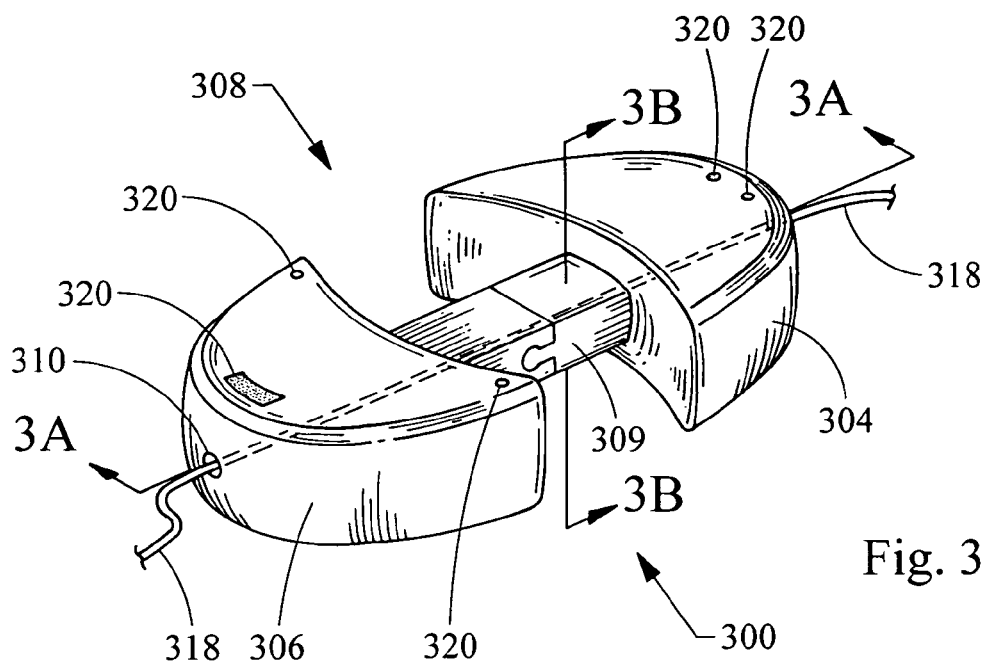
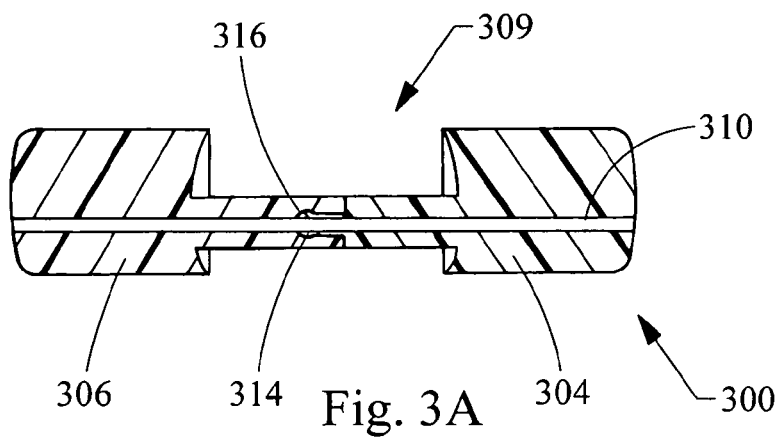
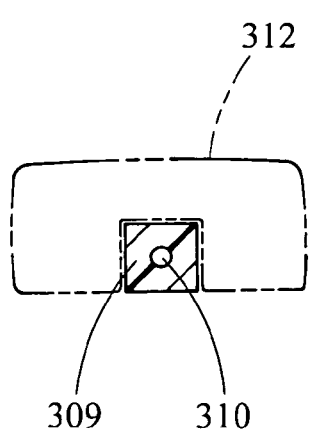 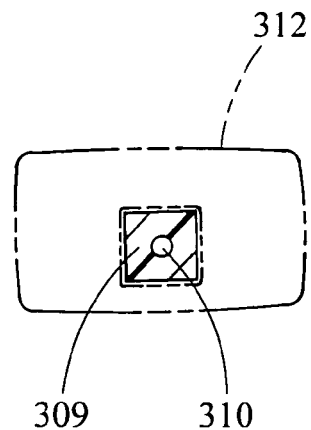

OBJECT-DELIVERY SHUTTLE

CROSS-REFERENCE TO RELATED APPLICATIONS

This application claims priority to U.S. Provisional Application Ser. No. 60/674,632, filed Apr. 25, 2005, which is incorporated herein by reference in its entirety.

FIELD OF INVENTION

The present invention relates to medical devices for use with a wire guide. More specifically, the present invention relates to a device and method for delivering objects along a wire guide or other elongate medical device.

BACKGROUND

Objects as varied as medicine tablets and data-gathering devices are typically delivered into the primary gastrointestinal passage of the body by swallowing. Such objects may also be placed surgically into selected locations in the body. However, each of these methods has limitations and drawbacks. For example, swallowed items generally have a limited dwell time within the body before being eliminated and are either dispersed throughout the body after absorption into the bloodstream (if soluble/absorbable) or are confined to the primary gastrointestinal passage. However, there are body locations outside of the primary passage of the gastrointestinal tract where it may be advantageous to place various medical devices/objects. Open surgical techniques can be used for such placement, but present well-known risks including surgical process trauma/stress to the patient body and the likelihood of infection. Therefore, there is a need for a device and method for delivering objects into passages of the body.

BRIEF SUMMARY

The above-mentioned needs are addressed by embodiments of the present invention, which are suitable for use with minimally invasive surgical techniques such as endoscopic surgery techniques as well as in conjunction with traditional surgical techniques.

In one aspect, the present invention includes an object-transport device for shuttling an object along an elongate medical device to carry or deliver an object within a patient body. The object-transport device has a body including a leading portion, a trailing portion, a cargo-carrying portion adapted to receive at least one object, and an aperture configured for slidably mounting the body onto an elongate medical device. In another aspect, the present invention includes an object-transport device for shuttling an object along an elongate medical device wherein the object-transport device has a body including a leading portion, a trailing portion, a cargo-carrying portion adapted to receive at least one object, and an attachment site configured for mounting the body to an elongate medical device.

In yet another aspect, the present invention includes a system for delivering an object into a patient body that incorporates a wire guide and a body that has a leading portion, a trailing portion, a cargo-carrying portion configured to receive an object, an aperture for slidably mounting the body onto the wire guide. The body also includes an object removably attached to its cargo carrying portion. The system preferably also includes a push-pull element for directing the body along the wire guide.

In still another aspect, the present invention includes a method for delivering an object to a site within a patient body. The method includes the steps of providing an object to be delivered and an object-transport device, said device comprising a body including a leading portion, a trailing portion, a cargo-carrying portion adapted to receive an object, and an aperture configured for slidably mounting the body onto a wire guide; attaching the object to the cargo carrying portion; mounting the device to the wire guide; and directing the device over the wire guide to a target site within a patient body.

BRIEF DESCRIPTION OF THE DRAWINGS

FIGS. 3-3C illustrate a third embodiment of an object-delivery shuttle;

DETAILED DESCRIPTION

Figure 1:
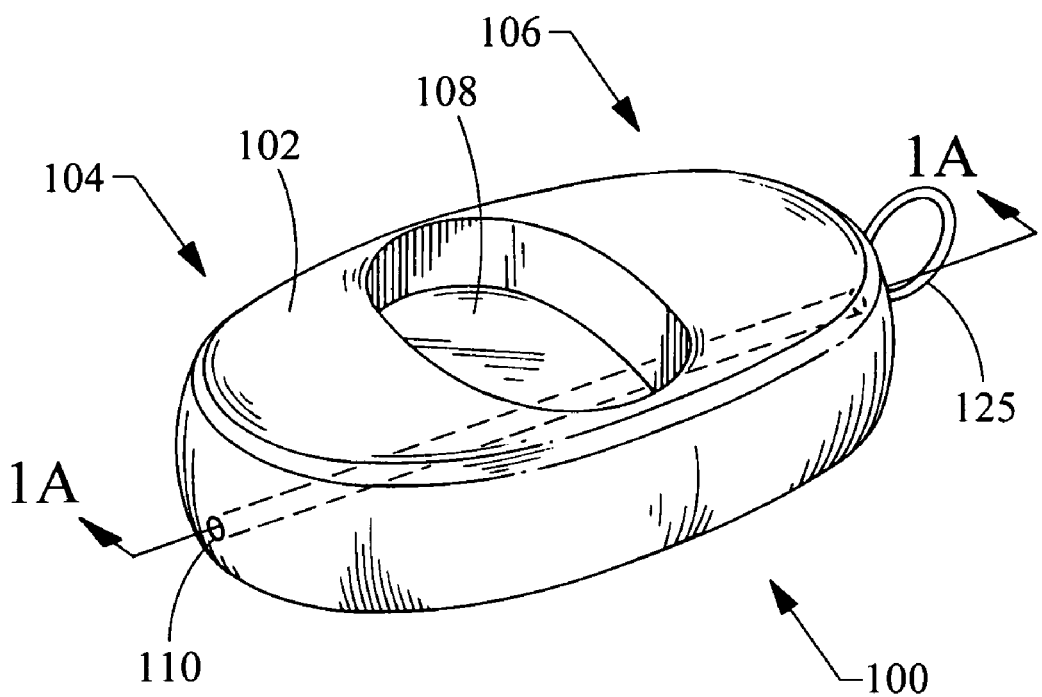
FIGS. 1 and 1A show a first embodiment of an object-delivery shuttle.
Figure 1A:
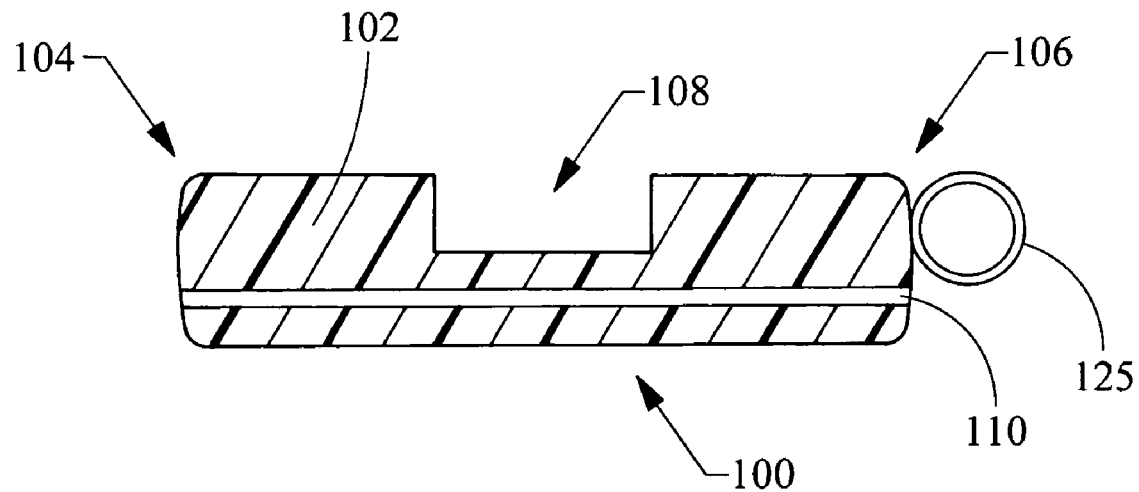

FIGS. 1 and 1A depict a first embodiment of an object-delivery shuttle 100. FIG. 1 is a perspective view of the shuttle 100. FIG. 1A is a longitudinal cross-sectional view along line 1A-1A of FIG. 1. The body 102 of the shuttle 100 includes a leading side 104, a trailing side 106, and a cargo-carrying portion 108. The leading and trailing sides 104, 106 are rounded to present a minimally traumatic profile, including a rounded external end surface as shown in FIGS. 1-1A, that minimizes sharp edges and friction, thereby easing passage of the shuttle along a wire guide through a desired path (e.g., working lumen of an endoscope, catheter lumen, endovascular or other lumen in a patient body). In alternative embodiments, the leading and trailing sides 104, 106 may be even more rounded (e.g., so as to present a semi-circular or semi-elliptical appearance).

The cargo-carrying portion 108 is configured to receive an object (not shown) to be delivered along a wire guide or other elongate medical device, such as a catheter. The object may be secured into the cargo-carrying portion 108 with a snap-fit, an appropriate adhesive, or some other appropriate substance, mechanism, or combination thereof.

A wire guide lumen 110 extends through the body 102 along the longitudinal axis. The body 102 may be constructed of a variety of materials depending upon the desired application. For example, the shuttle body 102 may be constructed of a resorbable or digestible material for an application where it is desirable or most convenient for a user to leave the shuttle 100 in a patient's body. In such an embodiment, the resorbable material could include a medicative substance such as a drug or other compound useful in treatment of the patient. As another example, the body 102 may be constructed of a non-resorbable metal, ceramic, composite, or plastic composition for applications where it is desirable or convenient to retrieve the shuttle 100 after use, or when the shuttle 100 is placed such that it can be naturally eliminated from the body.

For example, a non-resorbable shuttle device released in the gastrointestinal tract may be collected when it is eliminated along with bodily waste. Likewise, an appropriately shaped and appropriately placed shuttle may be used in a bile duct where the flow of bile will transport it into the gastrointestinal tract for elimination. As another example, a non-resorbable shuttle including a magnet or magnetic material may be recovered using a magnetic tool, or using a retrieval structure such as a loop 125 that can be captured, for example, by a hook-ended retrieval catheter, a snare, or a forceps. A shuttle having a non-resorbable composition may be configured to be sterilizable for re-use or may be constructed for single use and disposal. As one alternative, the shuttle may be coated with a material having properties useful in treating a patient (e.g., a drug) and/or may incorporate materials having properties useful in delivering the shuttle and its cargo to a target site (e.g., a radio-opaque marker for tracking, a lubricant, an anti-inflammatory agent, a hydrophilic coating).

Shuttle devices of the present invention may be configured for use in a variety of applications. For example, a shuttle may be used to transport a data collection device (e.g., a camera, pH monitor, radiometric device, or other device including MRI-compatible devices) to a portion of the biliary ducts between the duodenum and the liver, where such a device could not be positioned if merely swallowed. In such an application, the shuttle and the data collection device: (1) can both be left in the biliary duct for later collection; (2) can be mounted into the shuttle with an adhesive that dissolves in the biliary duct or a mechanism, both configured to release the device to allow immediate retrieval of the shuttle and subsequent retrieval of the data collection device at a later time; or (3) may be constructed of fractionable, digestible, soluble, and/or resorbable material, such that it is left in the biliary duct, with the device being later collected after the shuttle has been broken up, dissolved, and/or resorbed. As another example, a shuttle of the present invention may be used to deliver a time-release tablet, capsule of a drug, liquid- or gel-filled structure or other substance to a location reachable with a wire guide (or other elongate medical device such as a catheter or elongate stylet) that is not otherwise readily accessible to such a tablet or capsule. In such an application, the tablet, capsule, or other object being delivered preferably is digestible, fractionable, soluble, and/or resorbable. As yet another example, a shuttle of the present invention may be used to deliver magnets to sites in the gastrointestinal tract for use in creating an anastomosis therein such as is described in U.S. Pat. No. 5,690,656, owned by Cook, Inc. (Bloomington, Ind.), which is incorporated herein by reference. As still yet another example, the lumen 110 may extend through only a portion of the shuttle body 102, exiting through the top, bottom, or side to allow different cargo-carrying configurations and/or applications of the shuttle 100.

Figure 2:
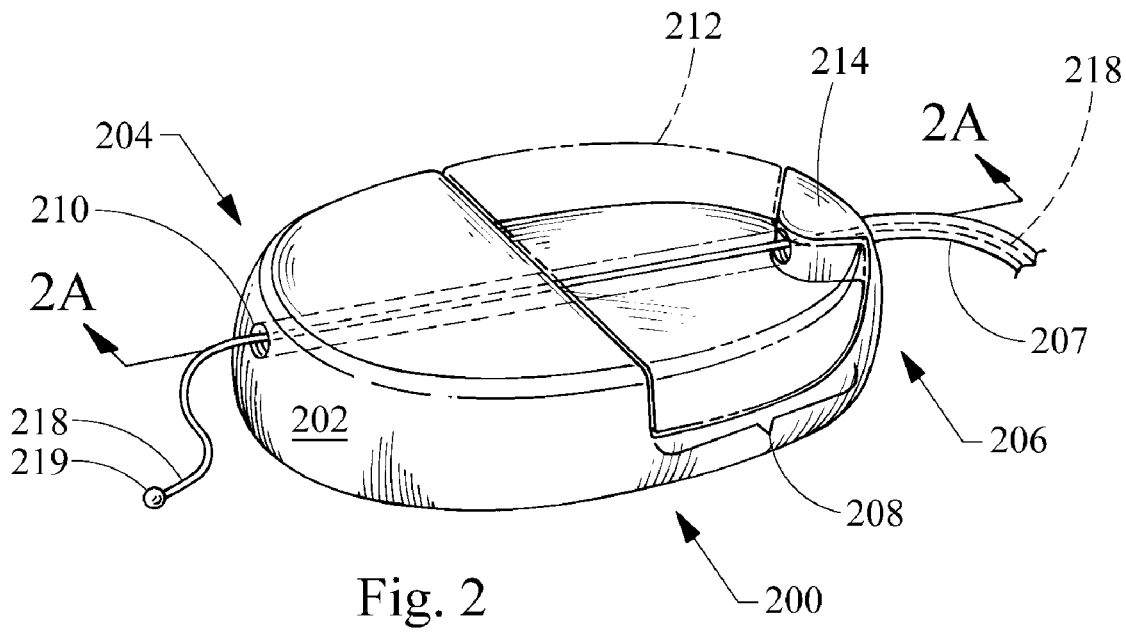
FIGS. 2-2C depict a second embodiment of an object-delivery shuttle.
Figure 2A:
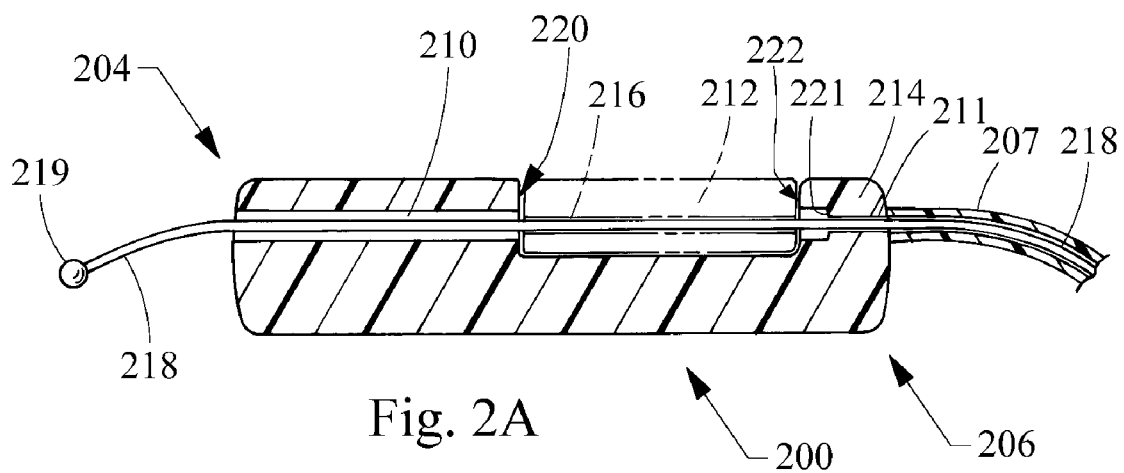
Figure 2B:
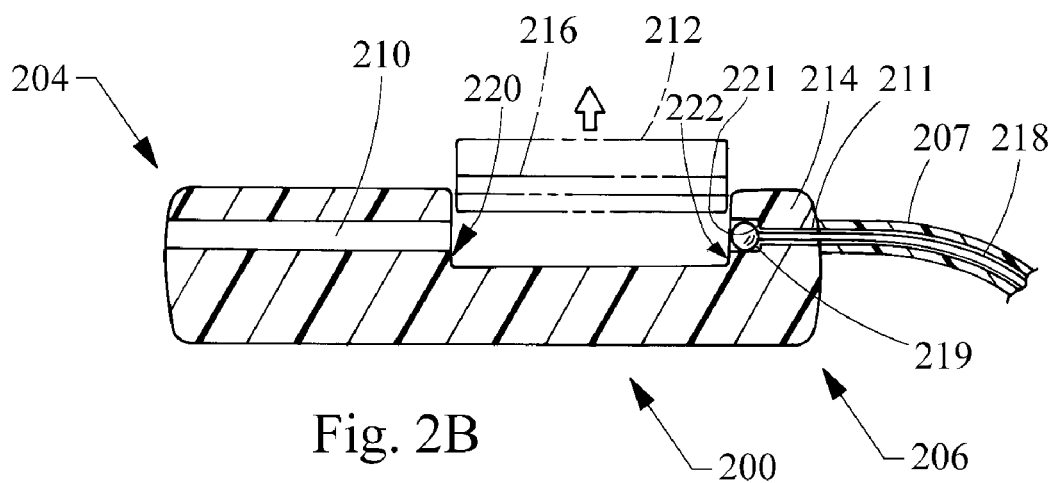

FIGS. 2, 2A, and 2B illustrate a second embodiment of an object-carrying shuttle 200. FIG. 2 is a perspective view of the object-carrying shuttle 200. FIGS. 2A and 2B depict longitudinal cross-sectional views along line 2A-2A of FIG. 2. The body 202 of the shuttle 200 includes a distal leading side 204, a proximal trailing side 206, and a cargo-carrying portion 208. The distal leading and proximal trailing sides 204, 206 are rounded to present a minimally traumatic profile that minimizes friction and sharp edges, thereby easing passage of the shuttle along a wire guide through a desired path (e.g., working lumen of an endoscope, catheter lumen, lumen in a patient body).

Figure 2C:
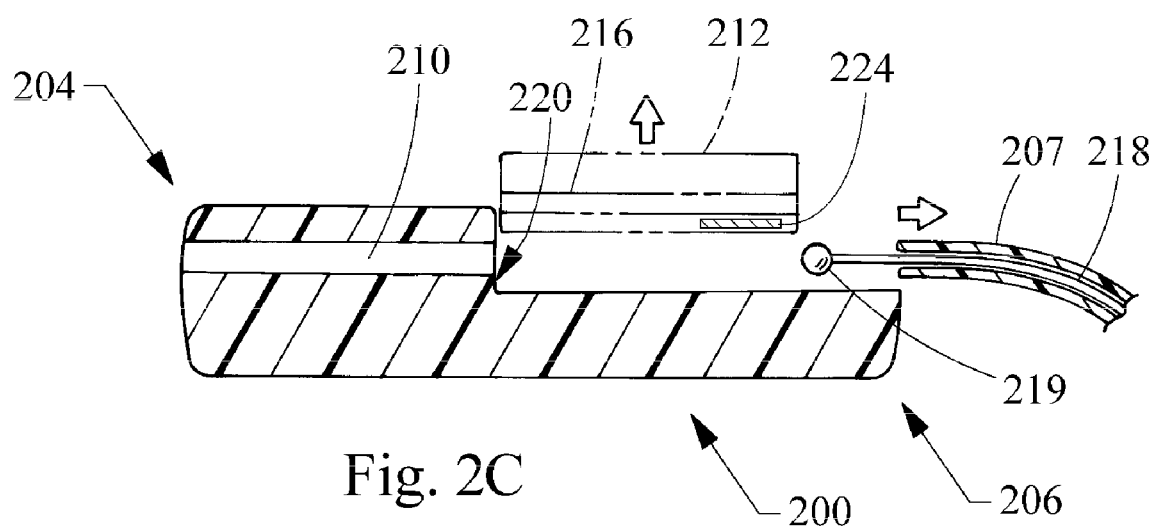

The cargo-carrying portion 208 is located proximally on the body 202 such that an object 212 (shown in phantom lines) to be shuttled effectively forms part of the proximal trailing side 206 of the shuttle 200. The structural portion trailing side 206 (that is part of the shuttle body 202) includes a projection 214 that forms a proximal side of the cargo-carrying portion 208 and helps to retain the object 212. Specifically, the cargo-carrying portion 208 includes a region defined on at least one end by at least one of a proximal surface 220 of the leading portion 204 or a distal surface 222 of the trailing portion 206, where the object 212 is retained. As shown in FIGS. 2A-2C, that region is substantially open (that it, a significant proportion of the cargo-carrying portion 208 is not bounded or otherwise defined by a physical structure other than on at least one end by at least one of a proximal surface 220 of the leading portion 204 or a distal surface 222 of the trailing portion 206, the same being true for the embodiments shown in FIGS. 1-1A, 3-3C, 4-4A, and 5A-5C). A wire guide 218 extends through a distal wire guide lumen 210, which itself extends from the leading portion 204, through the body 202 to the cargo-carrying portion 208. An introducer element embodied as a pusher 207 contacts the projection 214 and is configured for pushing the shuttle 200 along the wire guide 218. The pusher 207 may be removably or permanently attached to the projection 214.

The shuttle 200 is configured for use with an object 212 that has an object wire guide lumen 216 or is otherwise configured to be mounted to the shuttle 200 with a wire guide 218 in place. A proximal wire guide lumen 211 extends through the projection 214. The wire guide 218 acts to secure the object 212 in the cargo-carrying portion 208 when the wire guide 218 extends though the length of the shuttle 200.

One example of a mechanism for releasing the object 212 while retaining the shuttle 200 on the wire guide 218 is also illustrated in FIGS. 2A-2B. The wire guide 218 includes a radio-opaque bead 219 disposed on its distal end. The outer diameter of the bead 219 is smaller than the inner diameters of the wire guide lumen 210 and the object wire guide lumen 216, but is larger than the inner diameter of the proximal wire guide lumen 211. As shown in FIG. 2B, the wire guide 218 may be withdrawn through most of the length of the shuttle 200 (or a distal portion of the shuttle 200 may be advanced past the distal end of the wire guide 218, using the pusher 207). Once the bead 219 at the distal end of the wire guide 218 is withdrawn through the object lumen 216, the wire guide 218 no longer retains the object 212 in the cargo-carrying portion 208. A resilient mechanism such as a spring (not shown) may be provided in or on the lower surface of the cargo-carrying portion 208 to exert sufficient force to eject the object 212 from the cargo-carrying portion 208 when the wire guide 218 no longer extends through the object 212. A bead-receiving cavity 221 is provided in the distal side of the projection 214 and allows the bead 219 to be withdrawn completely from the object lumen 216 while still engaging the shuttle 200. As shown in FIGS. 2-2B, the object 212 is released intact. After the object 212 is released, the shuttle 200 (still engaged by the bead 219 at the distal end of the wire guide 218) may be retrieved along with the wire guide 218.

Alternatively, the object 212 may be retained in the cargo-carrying portion 208 by some chemical, mechanical structure such as a releasable latch, or other mechanism such as, for example, an adhesive, a friction fitting, or a magnetic connection. Such an attachment mechanism may be configured for releasing the object 212 at a target site. In an alternative embodiment, the projection 214 is not included. FIG. 2C shows an embodiment of the shuttle 200 where a projection 214 is not included. The cargo-carrying portion includes a substantially open region defined by a proximal surface 220 of the leading portion 204 where the object 212 is retained. The object 212 is configured to include a magnet 224. As shown in FIG. 2C, the object 212 is being released from the shuttle 200 and the shuttle 200 is being released from the wire guide 218 and the introducer/pusher 207.

FIGS. 3-3C illustrate a third embodiment of an object-delivery shuttle 300. FIG. 3 is a perspective view of the shuttle 300. FIGS. 3B and 3C each show a cross-sectional view along line 3B-3B of FIG. 3, and include an object 312 to be shuttled (shown in phantom lines in FIGS. 3B-3C; not shown in FIG. 3). The shuttle 300 includes a proximal end portion 304, a distal end portion 306, and a cargo-carrying portion 308. The proximal and distal end portions 304, 306 are rounded to present a minimally traumatic profile that minimizes sharp edges and friction, thereby easing passage of the shuttle along a wire guide through a desired path (e.g., working lumen of an endoscope, catheter lumen, lumen in a patient body). The central cargo-carrying portion 308 includes a central spine member 309 connecting the distal end portion 306 to the proximal end portion 304. A wire guide 318 extends through a longitudinal wire guide lumen 310, which extends from the distal end portion 304 through the spine member 309 to the proximal end portion 306. The surface of the shuttle 300 includes a set of radio-opaque markers 320, which are useful for locating and/or navigating the shuttle 300 when it is in a patient's body.

As illustrated in FIG. 3A, which is a partial longitudinal cross-sectional view of the shuttle 300 along line 3A-3A of FIG. 3, the shuttle 300 has a two-piece "snap-together" construction. The proximal portion of the central spine member 309 includes an engagement tab 314 and the distal portion of the central spine member 309 includes an engagement cavity 316 that complementarily engages the engagement tab 314.

The cargo-carrying portion 308 is configured to be able to retain the object 312 in several ways. For example, the object 312 may be attached by a mechanical friction fit between the proximal and distal end portions 306, 304, or it may be secured to one or both of the end portions 304, 306 by an adhesive or some other mechanism (e.g., a magnetic mounting). Alternatively, and as shown in FIG. 3B, the object 312 may be retained in the cargo-carrying portion 308 by a surface engagement with the spine member 309. This engagement may be accomplished, for example, by one of the attachment methods mentioned above (e.g., adhesive, snap-fit, magnetic) or some other method. As another alternative, depicted in FIG. 3C, the object 312 may have a cavity or passage therethrough that allows the central spine member 309 to extend through the object (by engaging the two portions 304, 306 of the shuttle 300 together through the cavity). This application is well-suited for use of the shuttle 300 with a soluble object 312.

Figure 4:
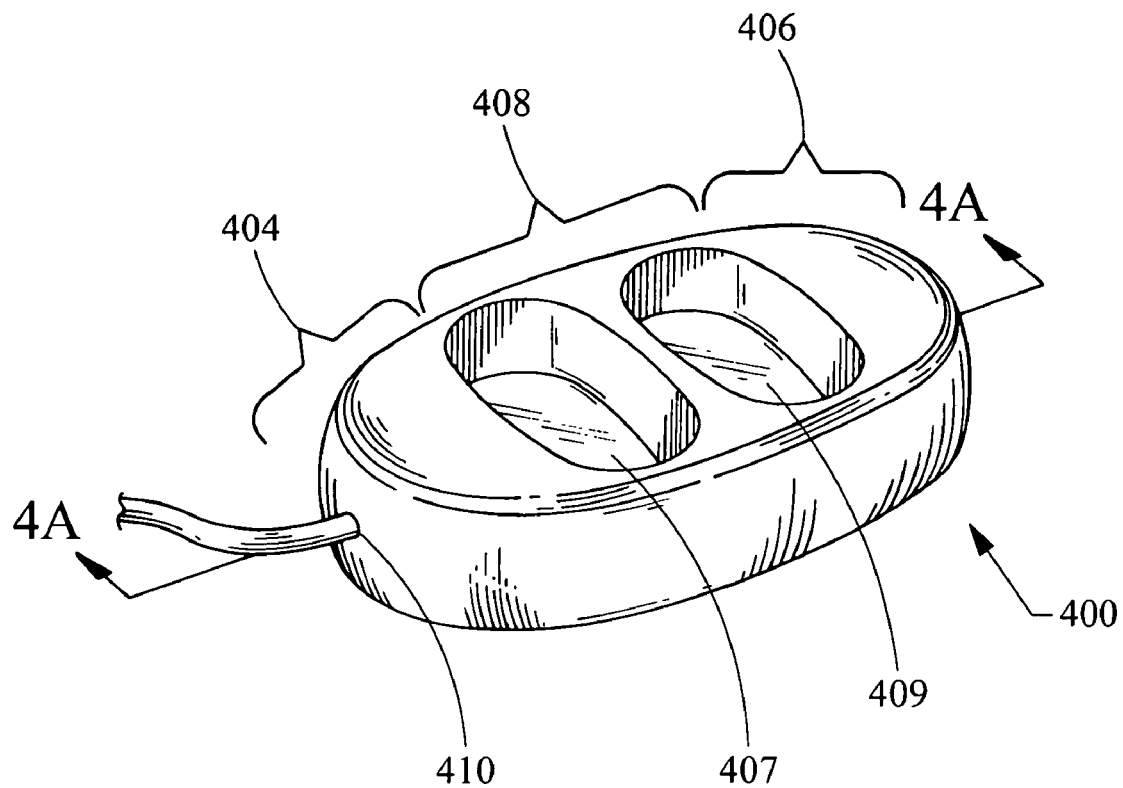
FIGS. 4 and 4A show a fourth embodiment of an object-delivery shuttle.
Figure 4A:
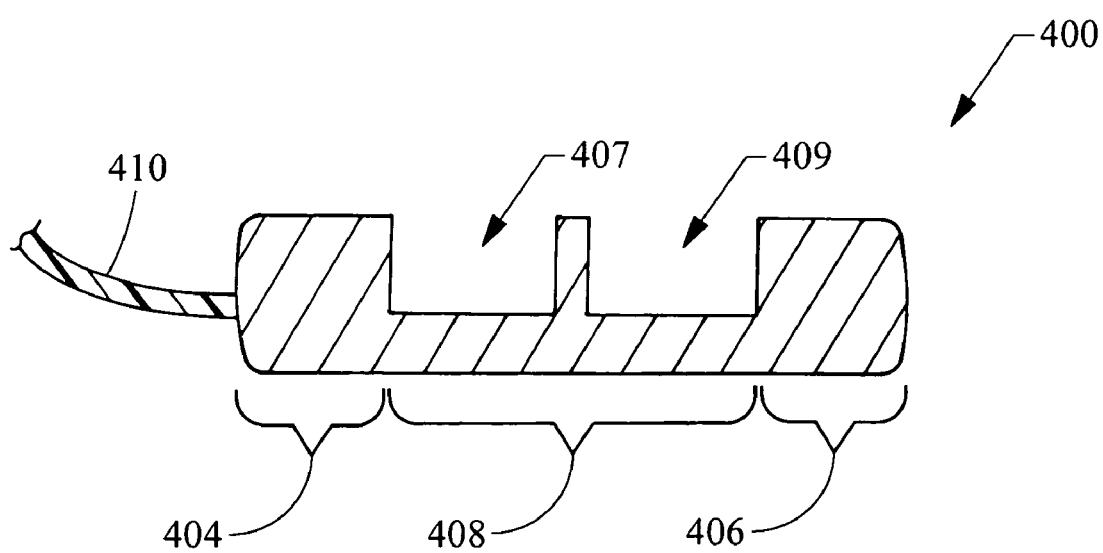

FIGS. 4-4A illustrate a fourth embodiment of an object-transport shuttle 400. FIG. 4 is a perspective view of the shuttle 400. FIG. 4A is a cross-sectional view along line 4A-4A of FIG. 4. The shuttle 400 includes a first end portion 404, a second end portion 406, and a cargo-carrying portion 408 therebetween. The cargo-carrying portion 408 includes two cargo compartments 407, 409. The first and second end portions 404, 406 preferably are rounded to present a minimally traumatic profile that minimizes friction and sharp edges, thereby easing passage of the shuttle along a wire guide through a desired path (e.g., working lumen of an endoscope, catheter lumen, lumen in a patient body). An introducer element embodied as a flexible pusher stylet 410 (which may include, for example, an elongate catheter of a length suitable to direct the shuttle 400 through a duodenoscope to the biliary tree of a patient) is attached to the first end portion 404. The engagement of objects to be transported may be accomplished, for example, by one of the attachment methods mentioned above (e.g., adhesive, snap-fit, magnetic, threaded connection) or some other method.

Figure 5A:
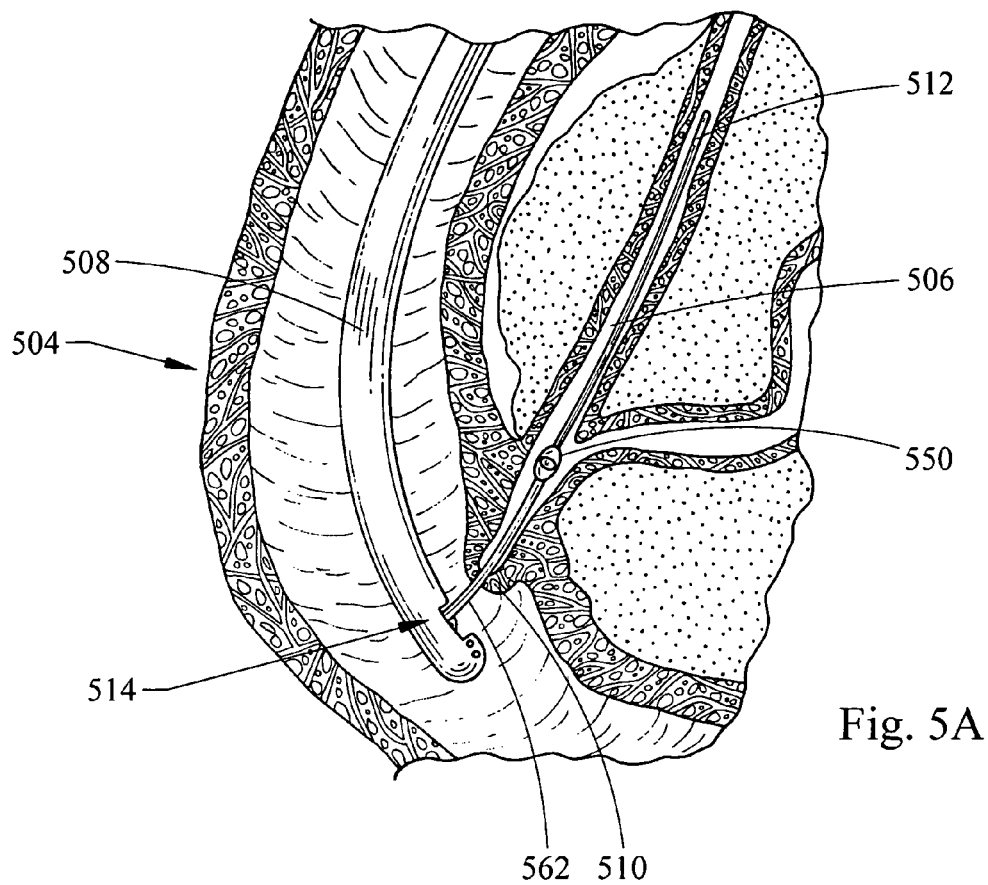
FIGS. 5A-5C illustrate a method of using an object-delivery shuttle.
Figure 5B:
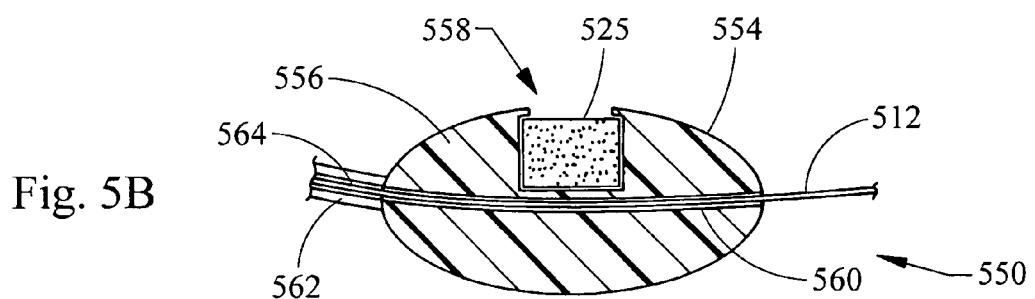
Figure 5C:
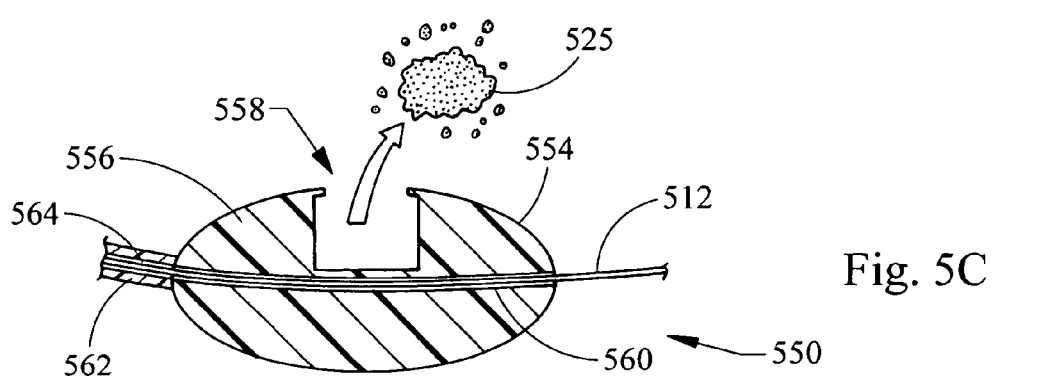

In another aspect, the present invention includes a method for using an object-delivery shuttle of the present invention to deliver an object. One example of the method is the delivery of a soluble drug tablet to the common biliary duct of a patient. The soluble drug tablet could be, for example, an anti-inflammatory pharmaceutical compound. FIGS. 5A-5C illustrate one embodiment of such a method. FIG. 5A is a line drawing of a duodenum 504 of a patient, showing a simplified diagrammatic view (not to scale) of a portion of the biliary system, including a bile duct 506. A duodenoscope 508 has been directed to a location in the duodenum 504 proximate the Ampulla of Vater 510, where the bile duct 506 enters the duodenum 504. The Ampulla of Vater 510 has been cannulated (e.g., with a wire guide, sphincterotome, or other mechanism), providing access for a wire guide 512 and an introducer element embodied as a catheter 562 to the bile duct 506. The wire guide 512 and catheter 562 extend through a working channel 514 of the duodenoscope 508. As shown in FIG. 5A, the wire guide 512 is dimensioned for passage through a working lumen of the endoscope 508 to the target site along a patient gastrointestinal tract (illustrated in the example of FIG. 5A as the biliary tree adjacent the duodenum 504), which is applicable to wire guides, stylets, cannulas, or other structures used with any embodiment herein along which a shuttle may be directed to a target site.

As shown in FIG. 5A, and in greater detail in FIGS. 5B-5C, an object-delivery shuttle 550 is provided. FIGS. 5B and 5C each depict a longitudinal cross-sectional view of the shuttle 550. The shuttle 550 includes a leading portion 554, a trailing portion 556, and a cargo-carrying portion 558. The leading and trailing portions 554, 556 are rounded to present a minimally traumatic profile that minimizes friction and sharp edges, thereby easing passage of the shuttle along a wire guide through a desired path (e.g., working lumen of an endoscope, catheter lumen, lumen in a patient body). The cargo-carrying portion 558 is configured to receive the soluble tablet 525. A shuttle wire guide lumen 560 extends through the shuttle 550 along its longitudinal axis. A soluble tablet 525 is secured in the cargo-carrying portion 558 by a frictional fit. The trailing portion 556 of the shuttle 550 is connected by adhesive to a pushing catheter 562 having a catheter wire guide lumen 564. A pusher other than a catheter may be used in variants of the present method and device. Also, in alternative embodiments, the pusher may have a releasable mechanical connection to the shuttle, such as, for example, a ball and socket connection.

The proximal end of the wire guide 512 is directed through the shuttle wire guide lumen 560 and the catheter wire guide lumen 564, and the pushing catheter 562 is used to push the shuttle 550 along the wire guide 512 through the working channel 514 of the duodenoscope 508, then through the cannulated Ampulla of Vater 510 and into the common bile duct 506. FIG. 5C presents the same detail view as FIG. 5B at a later time and illustrates that, after the shuttle 550 is in the bile duct 506, the tablet 525 dissolves and/or fragments. The dissolution and/or fragmentation of the tablet 525 reduces the size of the tablet 525, releasing the frictional fit so that the tablet 525 is released in the bile duct 506 to finish dissolving. The pushing catheter 562 is withdrawn from the duct 506 along with the shuttle 550. In alternative embodiments, the shuttle may be releasably attached to a pusher and may be left in the body.

The "leading" and "trailing" portions of the embodiments described above may be reversed in alternative embodiments. Placement of the wire guide lumen may also be varied. Those of skill in the art will recognize that other different configurations and variations of the object-delivery shuttle device, system, and method described and claimed herein are within the scope of the present invention. It is therefore intended that the foregoing detailed description be regarded as illustrative rather than limiting, and that it be understood that it is the following claims, including all equivalents, that are intended to define the spirit and scope of this invention.

I claim:

1. An object-transport device for shuttling an object along an elongate medical device within an internal lumen of a patient body, said object-transport device comprising:
    a body including
        a leading portion and a trailing portion, each comprising a minimally traumatic profile including a rounded external end surface configured for entry into and passage through a patient gastrointestinal tract;
        a lumen configured for slidably mounting the body onto one of a wire guide, catheter, or stylet and the lumen configured for the body to be shuttled along a complete length thereof, wherein said complete length is sufficient to be directed through an endoscope to a biliary tree of a patient;
    a cargo-carrying portion configured to releasably receive at least one object to be transported in, and released intact from, a substantially open region of the cargo-carrying portion defined on at least one end by at least one of a proximal surface of the leading portion and a distal surface of the trailing portion; and
    at least one object configured to be transported in the substantially open region and to be released intact therefrom.

2. The object-transport device of claim 1, further comprising an attachment structure for attachment of the body to an introducer device.

3. The object-transport device of claim 2, wherein the attachment structure provides a releasable attachment to the introducer device.

4. The object-transport device of claim 1, wherein the object-transport device comprises a material configured to be passed substantially undigested through a patient's gastrointestinal tract.

5. The object-transport device of claim 1, wherein the object-transport device comprises a material configured to be at least one of digestible, soluble, resorbable, and fractionable within a patient's body.

6. A method for delivering an object to a site in a patient body, comprising the steps of:
    providing the at least one object to be transported and an object-transport device according to claim 1;
    attaching the at least one object to the cargo-carrying portion, such that at least a portion of the at least one object occupies the substantially open region of the cargo-carrying portion defined on at least one end by at least one of a proximal surface of the leading portion and a distal surface of the trailing portion;
    mounting the object-transport device to the one of a wire guide, catheter, or stylet by directing the one of a wire guide, catheter, or stylet through the lumen; and
    directing the object-transport device over the one of a wire guide, catheter, or stylet to a target site in a patient body along its gastrointestinal tract.

7. The method of claim 6, wherein the object-transport device comprises a material having a property selected from the group consisting of digestible, soluble, resorbable, and fractionable.

8. The method of claim 6, wherein the at least one object comprises a material having a property selected from the group consisting of digestible, soluble, resorbable, and fractionable.

9. The method of claim 6, wherein the object-transport device further comprises an introducer element attached to the body and configured for moving the object-transport device over the one of a wire guide, catheter, or stylet during the directing step.

10. The method of claim 9, wherein the introducer element comprises an elongate catheter.

11. The method of claim 6, wherein an introducer element is releasably attached to the body of the object-transport device.

12. The method of claim 11, further comprising a step of releasing the body of the object-transport device from the introducer element.

13. The method of claim 6, wherein the step of directing the object-transport device over the one of a wire guide, catheter, or stylet comprises providing an endoscope with a wire guide placed therethrough, said wire guide being directed to the target site.

14. The object-transport device of claim 1, wherein the at least one object to be shuttled comprises at least one magnet.

15. A system for delivering an object into a patient body comprising:
    a wire guide dimensioned for passage through a working lumen of an endoscope to a target site along a patient gastrointestinal tract;
    a body including
        a leading portion and a trailing portion, each comprising a minimally traumatic profile including a rounded external end surface configured for entry into and passage within an internal lumen of a patient body;
        a lumen configured for slidably mounting the body onto the wire guide in a manner allowing the body to be shuttled along a complete length thereof; and
        a cargo-carrying portion configured to releasably receive an object to be transported in a substantially open region of the cargo-carrying portion defined on at least one end by at least one of a proximal surface of the leading portion and a distal surface of the trailing portion; and
    an object attached to the cargo-carrying portion, and substantially disposed within the substantially open region and configured to be released intact therefrom.

* * * * *